(12) United States Patent
Doyle

(10) Patent No.: US 8,880,457 B2
(45) Date of Patent: Nov. 4, 2014

(54) METHOD AND SYSTEM FOR RECOMMENDING A DECISION BASED ON COMBINED ENTITY MODELING

(75) Inventor: Mark Doyle, Wexford, PA (US)

(73) Assignee: Allegheny-Singer Research Institute, Pittsburgh, PA (US)

( * ) Notice: Subject to any disclaimer, the term of this patent is extended or adjusted under 35 U.S.C. 154(b) by 447 days.

(21) Appl. No.: 13/289,335

(22) Filed: Nov. 4, 2011

(65) Prior Publication Data

US 2012/0117021 A1    May 10, 2012

Related U.S. Application Data

(60) Provisional application No. 61/410,697, filed on Nov. 5, 2010, provisional application No. 61/442,596, filed on Feb. 14, 2011.

(51) Int. Cl.
 *G06N 5/00* (2006.01)
 *G06F 1/00* (2006.01)
 *G06F 19/00* (2011.01)

(52) U.S. Cl.
 CPC ............ *G06F 19/345* (2013.01); *G06F 19/363* (2013.01)

USPC .................. 706/54; 600/4; 600/410; 324/309

(58) Field of Classification Search
 USPC .......................................... 706/54
 See application file for complete search history.

(56) References Cited

U.S. PATENT DOCUMENTS

| | | | |
|---|---|---|---|
| 2002/0072933 A1 | 6/2002 | Vonk et al. | |
| 2007/0161868 A1 | 7/2007 | Root | |
| 2008/0267861 A1 | 10/2008 | Lieu et al. | |
| 2009/0078875 A1* | 3/2009 | Rousso et al. | ........... 250/363.04 |
| 2011/0178359 A1* | 7/2011 | Hirschman et al. | ............... 600/4 |
| 2011/0182881 A1* | 7/2011 | Chin et al. | .................. 424/130.1 |

\* cited by examiner

*Primary Examiner* — Jeffrey A Gaffin
*Assistant Examiner* — Kalpana Bharadwaj
(74) *Attorney, Agent, or Firm* — Fox Rothschild LLP

(57) ABSTRACT

A method for improved, automated analysis of a data set improves the reliability of the data set by comparing the data set with a model of similar data. The method may be used in applications such as medical imaging, clinical trial participant selection, marketing, security, traffic control, and other applications.

20 Claims, 9 Drawing Sheets

METHOD AND SYSTEM FOR RECOMMENDING A DECISION BASED ON COMBINED ENTITY MODELING

RELATED APPLICATIONS AND CLAIM OF PRIORITY

This patent application claims priority to U.S. Provisional Patent Application No. 61/410,697 filed Nov. 5, 2010, entitled "Method of Analyzing and Improving a Data Set for Use in Making a Decision Informed by Combining Entities" and U.S. Provisional Patent Application No. 61/442,596, filed Feb. 14, 2011, entitled "Method of Analyzing and Improving a Data Set for Making a Decision Informed by Combining Intermodality Entities." The disclosures of each of these applications are incorporated herein by reference in their entireties.

BACKGROUND

Many professions rely on the decisions of skilled professionals in order to yield successful results. For example, during almost every patient visit, medical professionals must make decisions regarding whether or not to require a particular course of action for the patient. Based on the results of a test, a physician will typically decide whether to order additional tests, whether to recommend a course of treatment, or whether to maintain the status quo. In highly complex professions such as medicine, professionals may be faced with a vast quantity of data and have difficulty determining which of the data is relevant to a decision.

This disclosure relates to an improved method for analyzing data and improving decision-making processes.

SUMMARY

This disclosure relates to methods of analyzing data for improved decision-making. More specifically, this disclosure relates to a method for improved, automated analysis of a data set that serves as the basis for a human decision by improving the reliability of the data set. The method may be used in applications such as medical imaging, clinical trial participant selection, marketing, security, traffic control, and other applications.

In one embodiment, a method of recommending a medical course of action such as a medical test, treatment, or inclusion of one or more patients in a clinical trial includes receiving a test result and one or more background parameters for a patient. The medical test result has a numeric value and represents a measured observation of a portion of the patient's body using a first medical testing modality. Each background parameter represents a pre-existing status of the patient. The method identifying a potential recommendation for a medical course of action and accesses a decision-making model. The decision-making model includes a set of thresholds, wherein each of the thresholds represents at least one background parameter and a level at which a majority of historic patients were recommended for the medical course of action based on correlated test results from both the first medical testing modality and a second medical testing modality. The method selects a threshold that corresponds to the background parameter of the patient, and compares the numeric value of the medical test result to the selected threshold. If the method determines that the numeric value of the medical test result equals or exceeds the selected threshold, then in response to the determination it may recommend the medical course of action.

The method also may include developing the decision-making model by: (i) receiving a first data set of medical testing results corresponding to tests performed on a first set of patients using the first medical testing modality; (ii) receiving a first set of background parameters corresponding to the first set of patients; (iii) receiving a second data set of medical testing results corresponding to tests performed on the first set of patients using the second medical testing modality; (iv) receiving a second set of background parameters corresponding to the first set of patients; and (v) determining the decision-making model based upon the first data set, the second data set, the first set of background parameters, and the second set of background parameters, such that the model includes a plurality of parameter-dependent thresholds for medical testing results from either or both of the first medical testing modality and the second medical testing modality.

In the embodiments described above, the first medical testing modality and the second medical testing modality comprise tests that may each measure a same observation of a portion of a patient's body, or they may measure different observations. For example, the modalities may be cardiac nuclear single photon emission computed tomography and magnetic resonance imaging, and the medical course of action may be treatment of a perfusion deficit. In this example, the background parameter(s) may include an indication that the patient is taking a prescription drug, and/or data corresponding to the patient's blood pressure.

In some embodiments, the method also may include receiving additional medical test results for a set of additional patients, wherein each test result corresponds to the first medical testing modality. The method also may include receiving at least one background parameter each of the additional patients, identifying a potential recommendation for a medical course of action, and accessing the decision-making model. For each of the additional patients, the method may include: (i) selecting one of the thresholds that corresponds to the background parameter of the patient; (ii) comparing the numeric value of the medical test result for each additional patient to the patient's selected threshold; (iii) determining a subset of the additional patients for whom the numeric value of their medical test result equals or exceeds their selected threshold: and (iv) in response to the determining, recommending the medical course of action for the subset.

Any of the embodiments listed above may be implemented by a recommendation that includes a processor and a tangible, processor-readable memory holding program instructions. In an alternate embodiment a recommendation system may include a processor, memory and program instructions that instruct the processor to receive a test result that has a numeric value and which represents a measured observation of a portion of a subject using a first testing modality. The processor will receive at least one background parameter of the subject, identify a potential recommendation for a course of action for the subject, and access a decision-making model. The decision-making model includes multiple thresholds, wherein each of the thresholds represents at least one background parameter and a level at which a majority of historic subjects were recommended for the course of action based on correlated test results from both the first testing modality and a second testing modality. The processor will select a threshold that corresponds to the background parameter of the subject, and compare the numeric value of the test result to the selected threshold. If the processor determines that the numeric value of the test result equals or exceeds the selected threshold, then in response to the determining the processor may recommend the course of action.

DETAILED DESCRIPTION

Figure 1:
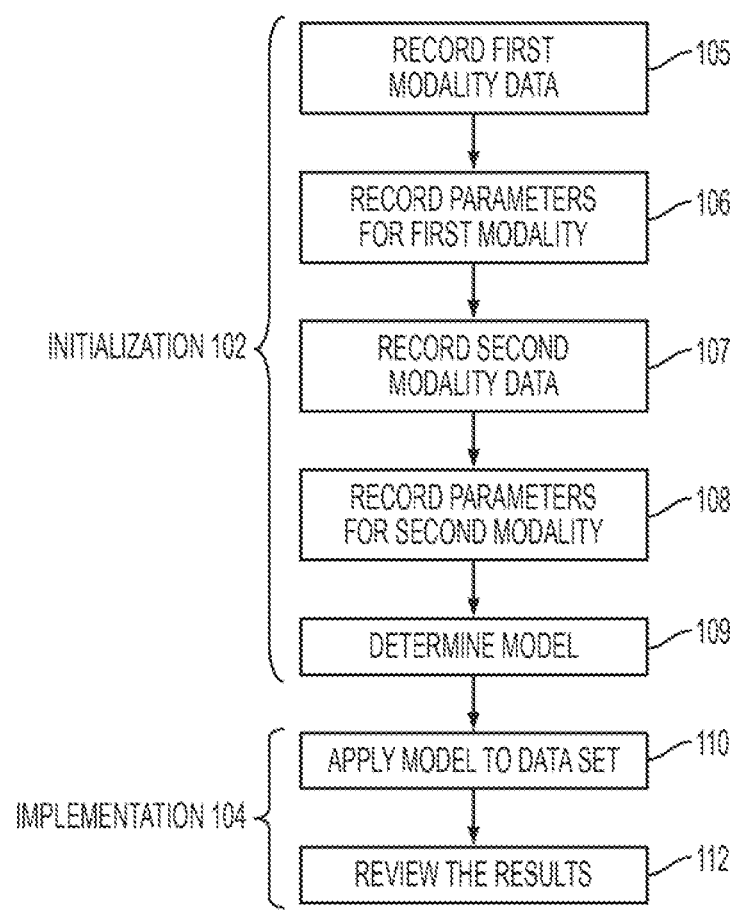
FIG. 1 is a flowchart showing a decision-making process according to an embodiment.

This disclosure is not limited to the particular systems, devices and methods described, as these may vary. The terminology used in the description is for the purpose of describing the particular versions or embodiments only, and is not intended to limit the scope.

As used in this document, the singular forms "a," "an," and "the" include plural references unless the context clearly dictates otherwise. Unless defined otherwise, all technical and scientific terms used herein have the same meanings as commonly understood by one of ordinary skill in the art. Nothing in this document is to be construed as an admission that the embodiments described in this document are not entitled to antedate such disclosure by virtue of prior invention. As used in this document, the term "comprising" means "including, but not limited to." As used in this document, the terms "sum," "product" and similar mathematical terms are construed broadly to include any method or algorithm in which a single datum is derived or calculated from a plurality of input data.

As used herein, the term "modality" refers to a mode, process or method of obtaining a set of data. For example, a modality may include a specific medical test or imaging process wherein one or more sets of patient specific data are obtained.

Typically, when a human makes a decision, the person relies upon some set of known facts or concrete evidence. However, this set of known facts may not include all necessary information required to make the decision. Thus, the person must use some amount of judgment when making the decision.

One example of an area where data set selection is important is the selection of participants for a clinical trial. New drugs are expensive to develop, and the regulatory approval process is also expensive and time-consuming. If a clinical trial's patient population happened to include a large population that was highly susceptible to a particular medical condition, the trial results may not accurately reflect the drug's ability to prevent that condition in the general population, and it may not sufficiently reveal potential side effects. On the other hand, if a goal of the trial is to measure the drug's effectiveness in high-risk patients, a trial population that is highly susceptible to the condition may be desirable. Thus, the decisions that result from a clinical trial outcome may be impaired if the clinical trial relied on a less than ideal data set.

Another example of such a decision may be the interpretation of a medical image. For example, nuclear single photon emission computed tomography (SPECT) images of the human heart require review and interpretation by a medical professional. However, nuclear SPECT images suffer from numerous sources of contamination, such as low intensity regions that are caused by varying tissue density. Generally, human judgment is required to decide whether a low intensity region on a cardiac SPECT image was caused by an actual perfusion deficit in the heart, or whether it was caused by a source of error such as a tissue attenuation artifact. Typically, several physicians review a SPECT image and form a consensus as to the results of the SPECT image.

In the case of medical imaging, it is sometimes possible to obtain further insight by obtaining additional information using a different means of collecting the information. In the example of cardiac SPECT, additional information can be obtained via cardiovascular magnetic resonance imaging (MRI) to additionally assess the perfusion data related to the heart. In a similar manner to SPECT imaging, a low intensity region may be present in the MRI information and require human interpretation and judgment to assign it to a region of perfusion deficit. Thus, both SPECT and MRI may suffer inaccuracies as a result of the necessary step of introducing human judgment to interpret the images that were obtained using two separate modalities.

Cardiac medical images have various uses, but typically these can be broken down into a diagnostic use and a prognostic use. Continuing the example above, the diagnostic use of SPECT images may be to identify a partially blocked coronary artery. This information may be used to determine a course of treatment based upon the clinician's interpretation of the evidence discovered in the images. However, the SPECT images also have a prognostic value, whereby the presence of a perfusion deficit detected by the modality indicates that the patient is at an increased risk of an adverse event (e.g., suffering a myocardial infarction), irrespective of whether the deficit corresponds to a localized partial or full blockage of a corresponding coronary artery. Thus, a patient with a SPECT image-identified perfusion deficit may receive intensified treatment due to an established diagnostic and prognostic value associated with the SPECT images. Those patients not judged to have a deficit are typically sent home without further treatment. These decisions are made by humans based upon their experience with patients or by studying the results of various clinical trials.

The manner of reading SPECT images has adapted to various clinical trials in that a certain percentage of those sent to a catheterization lab for further treatment have high-grade coronary artery narrowing or stenosis. Accordingly, a certain percentage of those with an identified perfusion deficit suffer an adverse event. However, while the rate of experiencing an adverse event is higher in the group identified as having a perfusion deficit, it is often the case that in absolute terms, due to the generally larger population, the absolute number of serious adverse events is higher in the group that a test identified as having no perfusion deficits.

By performing additional imaging such as MRI, the physician or physicians reviewing the SPECT images may have additional information on which to rely. However, additional testing is expensive and is often rejected by a patient's insurance carrier. Thus, the human judgment often must be limited to the results from a single modality of testing (e.g., either SPECT or MRI).

Human judgment is not limited to medical fields. Many fields require human judgment. For example, software applications often incorporate features that are included because of decisions made by the application's programmer. For example, the programmer may have selected a particular algorithm for analyzing a set of data. Based upon this decision, the results of the algorithm may be focused solely on an area selected by the programmer far in advance of the software application being released for public use.

One area where human judgment is included in software applications is statistical analysis. A set of statistics relating to a particular topic may be analyzed using one or more specific algorithms, and a set of results may be produced for use by another software application. For example, a social networking site may collect a large amount of statistical information relating to its users, such as age, sex, location, job, income level, education, and other information. A software application may analyze this statistical information to achieve various results. For example, a software application may analyze the statistical information to identify targeted advertising that may be of interest to a particular user. However, because the initial algorithm was chosen by the software programmer, the interpretation of the statistical information still includes some human judgment and may result in inaccuracies.

This document describes a process of making a decision informed by combining entities (DICE) and a decision informed by combining intermodality entities (DICIE). The DICE process may use a first data set obtained by a first modality in an area of interest, along with a second data set obtained via a second modality in the area of interest, to analyze the reliability of new data obtained by either of the two modalities. Each data set relates to the same condition of interest, such as the absence or presence of a particular medical condition. The two modalities are two different ways of measuring or assessing the subject. For example, a set of patients may be tested for heart disease using a first modality such as nuclear SPECT imaging. The information may be compared with results obtained from a second modality such as an MRI to create a model set. Then, when a new patient is analyzed using either SPECT or MRI, the new patient's data may be compared with the model set to assess the patient data's reliability or suitability for use as the basis for a decision by a medical professional, such as whether or not the patient should undergo a particular course of treatment for heart disease.

FIG. 1 illustrates a decision making process based upon DICE. The process may include two stages: initialization 102 and implementation 104. During initialization 102, a set of subjects may be tested or analyzed for a particular condition of interest using a first modality. The information obtained from this first modality, referred to in this document as a first data set, may be received and recorded 105. The first data set may include, for example, information obtained from a first modality that indicates the presence of heart disease in a set of patients (e.g., pixel-specific data from a SPECT image). The initialization process also may receive a set of parameters for the first data set, such as physiologic parameters (e.g., whether each patient has any other diseases), demographic (e.g., each patient's sex, age, race, geographic location, occupation), and/or concurrent image information, related to each subject (e.g., patient) in the first data set. The parameters may be recorded 106 into a database on a computer readable medium after they are received via an entry field on a DICE computer application or other similar data entry mechanism.

A second data set of information obtained from a second modality (e.g., pixel specific data from an MRI data set for the set of patients) may be received 107 and recorded 108 in a similar fashion.

Using the recorded parameters, a software application may instruct a processing device to determine 109 a mathematical model that indicates how the first set of data from the first modality (e.g., SPECT imaging) may be represented in a second modality (e.g., an MRI). A statistical application package may be used to determine 109 the mathematical model (i.e., mimicking or predicting results of the second modality using information obtained from the first modality) based upon a regression equation (e.g., a linear regression equation). The statistical application package may run as a stand-alone application, or it may be part of a DICE-related software package. Optionally, additional data sets may be collected from additional modalities and used in the model. For example, if echocardiograph data is also available for a portion of the patient population, a third data set and related parameters for echocardiography may be included in the model.

Figure 2:
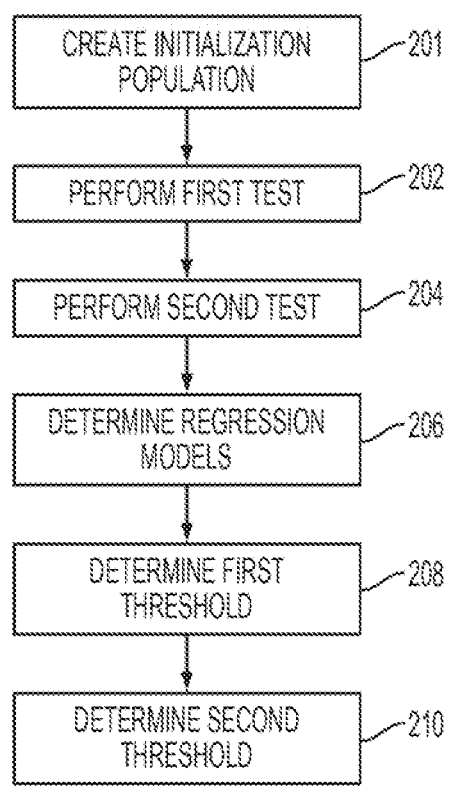
FIG. 2 is a flowchart showing a process for determining a mathematical model according to an embodiment.

FIG. 2 illustrates a process for determining 109 a mathematical model for predicting results of a specific modality. Initially, a test or initialization population may be created or identified 201. The initialization population may include subjects (e.g., patients) who have been or who will be analyzed using two or more of the modalities that were used to create the data set. For example, if three modalities (such as SPECT, MRI, and echocardiograph) may be used to produce a results set, each patient in the initialization population would have provided information relating to at least two of the modalities for comparison and prediction purposes.

To continue the above example, the initialization population may include patients who had both a cardiac SPECT examination and a cardiac MRI examination to identify potential perfusion deficits. If the tests have not already been performed, to create the first and second data sets, a physician may perform 202 the first test or modality (e.g., SPECT imaging of the patient's heart) on a member of the initialization population and examine the results. The physician may code the results of the first test as having a first value (e.g., positive or one) if the results are positive for a perfusion deficit, or a second value (e.g., negative or zero) if no perfusion deficits are found. Additional background parameters also may be collected such as physiologic or demographic information relating to the subject patient tested, such as age, sex, weight, height, blood pressure, and various physical measurements obtained from the image or set of images such as diastolic volumes of various chambers of the patient's heart.

For the same patient, the physician may perform 204 the second test or modality (e.g., MRI examination of the patient's heart). Again, the physician may code the results of the second test as having a value of one if the results are positive for a perfusion deficit, or zero if no perfusion deficits are found. The physician may also collect any additional information that may be obtained from the results of the second test. The testing process may be repeated for a number of patients (e.g., 500) to create an adequately sized initialization population. The information collected (i.e., the image data for each modality, the coded perfusion results and any collected parameters) may be processed and stored in a database on a computer readable medium. The database may be configured such that physicians from multiple hospitals and health care centers have access to the information.

Based upon the information related to the initialization population, the statistical software package may determine

206 one or more regression models for each test. For example, the software may load the information collected for each test subject (e.g., the results of both the cardiac SPECT examination and the cardiac MRI examination) and analyze the imaging data results (e.g., perfusion deficit present or perfusion deficit absent) and parameters to identify any patterns in the information related to what parameters correspond to perfusion deficits or the absence thereof. During the determination 206, the software may systematically enter and remove variables such as individual test subject parameters to determine whether any of the parameters correlate to any of the first data set (SPECT) results and/or second data set (MRI) results, using one or more linear regression equations. Through this process, the software may include or reject variables in the regression equation based on how the variables improve the fit of the regression model. For example, a 5% threshold may be set to allow a parameter to contribute to the model. If so, then if the existence of a parameter corresponds to the existence of a perfusion deficit in at least 5% of patients, it may be included in the regression model. This analysis may be repeated for other parameters, and the thresholds may be adjusted.

This regression process may result in two unique mathematical models, a first model for predicting the results of the second test based upon data obtained during the first test, and a second model for predicting the results of the first test based upon data obtained during the second test. Each model may include an equation that factors in whether the obtained results are positive or negative, one or more parameters that are found to be predictive of a positive or negative result in the other test (i.e., the test for which results are not available when applying the equation, but were present in the data set), and other variables or constants. For example, an equation to predict the results of an MRI evaluation of perfusion status based upon data obtained from a SPECT examination may be as follows:

$$\text{Model Prediction of MRI} = -0.01 + (0.3 \times \text{SPECT deficit}) + (0.05 \times \text{EDV}), \quad \text{Equation 1}$$

wherein:
"SPECT deficit" is set to (a) zero if no perfusion deficit was determined to be present in the SPECT image, or (b) one if a perfusion deficit was determined to be present in the SPECT image;
and
EDV=the end diastolic volume of the left ventricle as measured based upon a physician's or computer algorithm-directed reading of the SPECT image or images.

The model may generate a continuum of values based upon the constants used by the statistical application package. To be declared positive, a first threshold value may be set for the prediction value. The threshold value may be based upon an analysis of existing MRI and SPECT image information. For example, the software may determine 208 a first threshold based upon the average number of cases determined to be positive in the first test. This first threshold value may be used as the threshold value for the mathematical model for predicting the results using the second test. Similarly, the software may determine 210 a second threshold value based upon the average number of cases determine to be positive in the second test. This second threshold value may be used as the threshold value for the mathematical model for predicting the results using the first test.

To continue the above example, an average number of positive SPECT images in the initialization population may be used to determine 208 the first threshold (e.g., 0.38). Then, when predicting results of a SPECT model based upon data obtained from an MRI image, if the predicted results are above the first threshold (i.e., 0.38 in this example) the predicting SPECT model indicates a positive result. Similarly, an average number of positive MRI images in the initialization population may be used to determine 210 the second threshold (e.g., 0.35). Then, when predicting results of an MRI model based upon data obtained from a SPECT image, if the predicted results are above the second threshold (i.e., 0.35 in this example) the predicting MRI model indicates a positive result.

As shown above, the mathematical model may include additional parameters such as end diastolic volume of the left ventricle of the heart. However, this additional parameter is shown by way of example only and other parameters may be used.

Once the statistical software package determines 108 the mathematical model, the model may be applied 110 to the original or new data sets. It should be noted that at this stage actual data from only one modality is needed. For example, SPECT data obtained from a patient may be used to model an MRI result, regardless of whether an MRI was actually performed on that patient.

To continue the above example, results obtained from a SPECT image for a first patient may be entered into an equation that uses the SPECT results, a value corresponding to at least one parameter and optionally other variables or constants in an equation such as Equation 1 above to determine an MRI prediction value for that first patient. If the modeled MRI prediction value is greater than the associated MRI prediction threshold value, the process assumes that an MRI image for the first patient would produce a positive result (i.e., a perfusion deficit is present). Based upon the human reading of the data (e.g., SPECT data assessed to determine if a perfusion deficit is identified or not) and then entering this result into the model to predict the MRI result, and applying the threshold to obtain the modeled result, a physician may accept the result 112 to determine whether a perfusion deficit is identified in the data for the patient, or whether no significant perfusion deficits are identified for the patient data.

Thus, the methods disclosed above help identify patients who may be at risk and thus should be recommended to receive a medical course of action, such as additional testing, therapy, a prescription drug or surgical intervention. The recommendation is based on a combination of measured variables, including as the primary result of a measure of a diagnostic test. The recommendation also considers secondary variables, which may be measured by the primary diagnostic test or other test(s) or by known information about the patient such as the patient's age, sex, blood pressure, pre-existing medical conditions (such as diabetes) or whether the patient is taking a prescription drug. Thus, the same test may be administered to two patients, and the test results may be the same for the two patients, but the patients may receive different recommendations based on how each patient's background factors correspond to the model.

Thus, the methods described in this document may help to address a fundamental issue in healthcare delivery whereby some patients with test values below an accepted actionable threshold may be at risk for suffering an adverse event (e.g., heart attack, stroke, dying of cancer), but if the actionable threshold were universally lowered it would lead to overtreatment of many patients who were not initially at risk, with consequences for increased expense and treatment-related damage (e.g., inappropriate stenting of coronary arteries, inappropriate carotid artery plaque removal, inappropriate radical mastectomy). In addition, the methods may help identify and/or avoid any inherent bias that may be present in a testing modality. For example, if one imaging modality may work well with a patient group that has a first physical characteristic but not as well with a group that has a second characteristic, the methods described above may help eliminate any bias that may be inherent in the interaction of the imaging modality and the patient characteristic.

The modeling approach described above is not limited to models that use results from two testing modalities. For example, as illustrated in the hypothetical data chart of FIG. 3, a model may consider results from SPECT imaging along with quantitative MRI readings (designated as SQMRI) and qualitative MRI readings such as physicians' visual MRI interpretations (designated as QLMRI). In this hypothetical data set, the vertical y-axis shows the percentage of patients falling into each category for patients undergoing myocardial perfusion imaging. The left-right x-axis shows groupings of patients whose clinical test yielded a positive result for a myocardial perfusion deficit (expressed as a percentage of the full population of patients considered), the percentage of patients who experienced an adverse event but who tested negative for the presence of a myocardial perfusion deficit (expressed as a percentage of the patients who suffered an adverse event), and the percentage of patients who both tested positive and experienced an adverse event (expressed as a percentage of the patients who suffered an adverse event). The axis into the plane indicates the three clinical tests that were applied: SQMRI, QLMRI and SPECT. These results show that about 30% of patients who undergo myocardial perfusion imaging are found to possess a myocardial perfusion deficit, with a similar profile across the three modalities. However, about 60% of the severe adverse events (dominated by death and heart attacks) occurred in those patients who were cleared of having a myocardial perfusion deficit.

Figure 4:
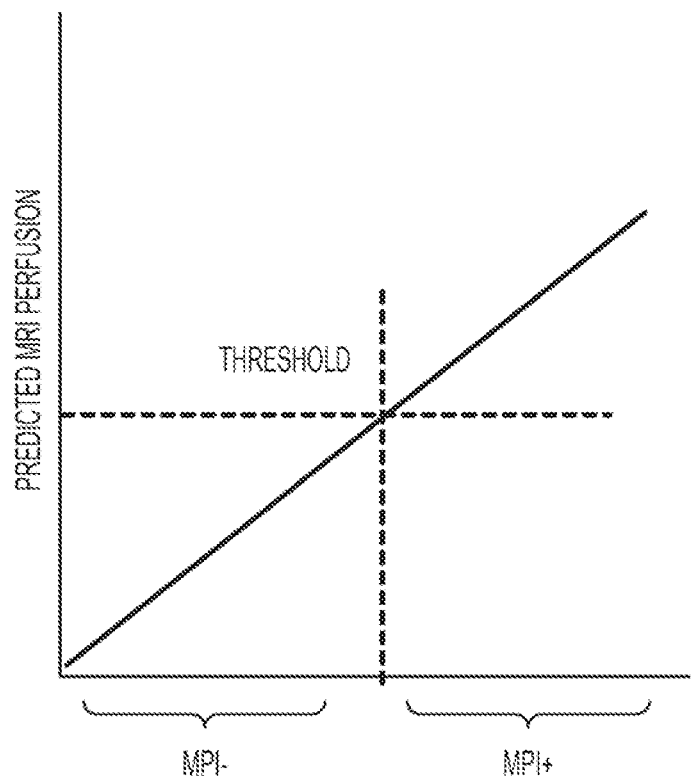
FIG. 4 illustrates how modeling may improve a decision-making process by separating patient populations across a threshold

To remedy this, FIG. 4 shows how modeling may improve a decision making process. Referring to FIG. 4, the vertical y-axis represents a regression model value obtained from one test predicting another. For instance, an MRI diagnostic test applied to obtain myocardial perfusion images (MPI) might be used to predict the results of a second diagnostic test such as nuclear SPECT. The horizontal x-axis represents the patient population. A threshold is set for the modeled MPI interpretation, such that those patients below the threshold are considered to be negative for myocardial perfusion disease (MPI−) and those above the threshold at considered to be positive for myocardial perfusions disease (MPI+). In this way, a single threshold may be set, but since the threshold is applied to the modeled data, the MPI+ patients contain a mixture of patients who would normally have been considered MPI+ by the conventional interpretation methods as well as patients who would normally be considered to be below the conventional threshold.

The processes discussed above may be extended to include other known risk factors. For example, if a known ailment such as high blood pressure is associated with adverse events such as coronary artery disease, the threshold of the model value may be varied depending on a patient's blood pressure. In the above example, by lowering the threshold for a patient with high blood pressure, the sensitivity of the modeling may be increased and additional high-risk patients may be identified. Thus, in a data rich environment, increasingly sophisticated use may be made of data modeled via the DICE process to make better human judgment decisions.

Figure 3:
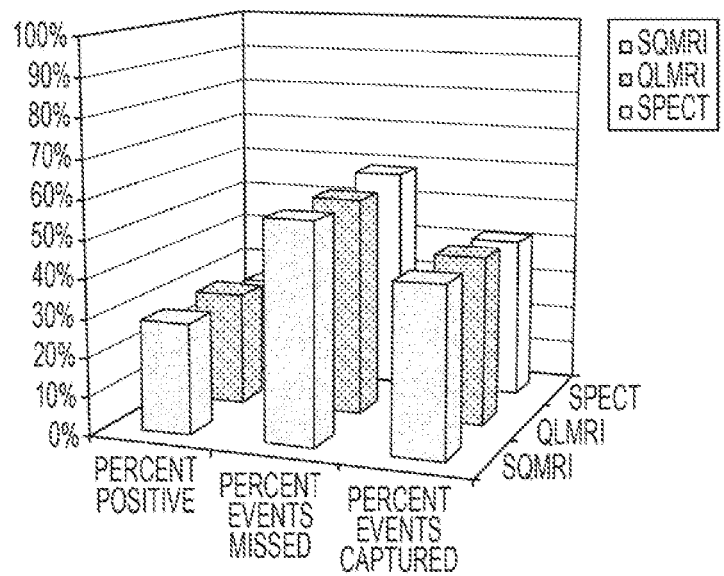
FIG. 3 illustrates a comparison of test results received via multiple testing modalities.
Figure 5:
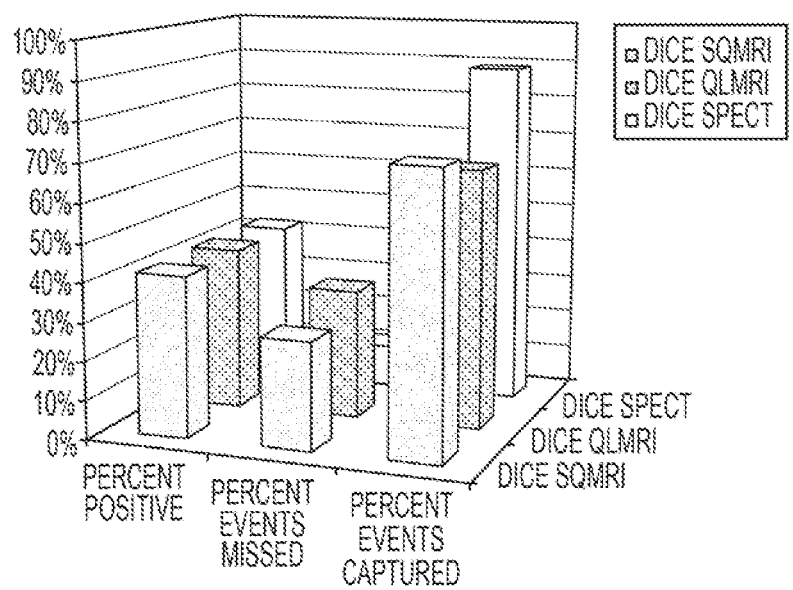
FIG. 5 illustrates the hypothetical test results of FIG. 3 after modeling is applied

FIG. 5 illustrates a modified version of FIG. 3 in which the modeling approach of FIG. 4 is applied to test results of patients undergoing myocardial perfusion imaging. In this case, for all three readings over two modalities, DICE was applied to redefine patients as having positive evidence of a deficit in their myocardial perfusion image (MPI+) which identified about 40% of patients as MPI+. 70-90% of the severe adverse events (dominated by death and heart attacks) occurred in the DICE identified MPI+ group.

Figure 6:
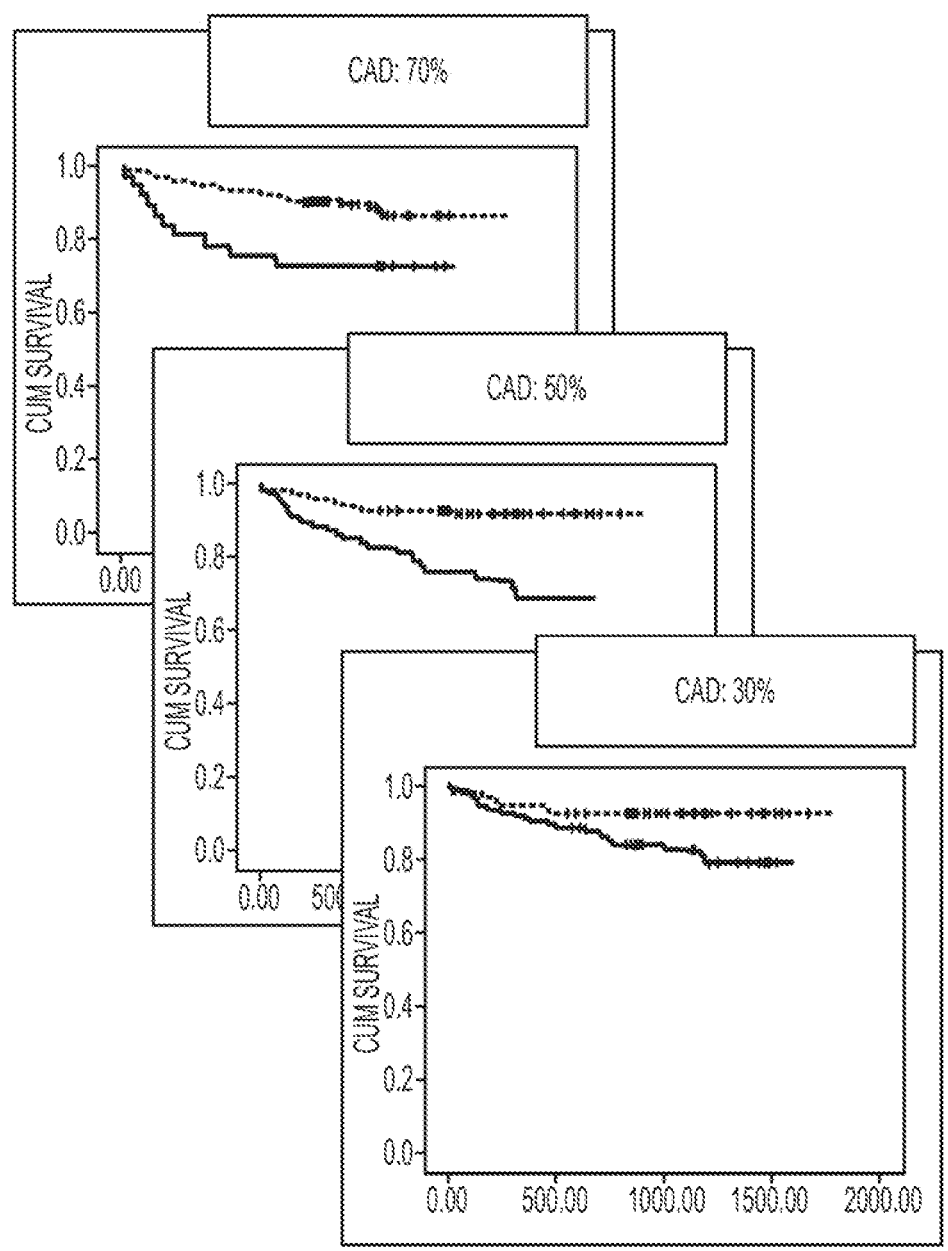
FIG. 6 illustrates how thresholds may be selected without the application of DICE or DICIE.

FIG. 6 shows three Kaplan-Meier plots showing threshold selections applied to coronary artery stenosis data without the application of DICE or DICIE. In each plot, the vertical y-axis shows the cumulative event-free survival percentage for each group, and the horizontal x-axis shows follow-up time (up to 5 years). For each plot, patients are grouped as above or below the threshold for coronary artery disease with thresholds selected at 70%, 50% and 30% stenosis. It can be appreciated that event-rates for patients thresholded at the 70% stenosis level are quite different between the patient groups. However, setting the threshold this high results in only identifying 30% of events in the "high disease" patients. Progressively setting the threshold of high disease to lower levels (a 50% threshold for stenosis captures 66% of events in high disease group, whereas a 30% threshold for stenosis captures 75% of events) results in more capture of disease, but at the expense of identifying progressively more patients as being at risk. Thus, while setting the threshold at 30% captures 75% of events in the high disease group, the majority of patients are classified as high disease, which may not be desirable to warrant aggressive treatment in such a large group, since a reason for performing a diagnostic test is to limit treatment to those who can potentially benefit, without subjecting those with lower levels of disease to treatment.

Figure 7:
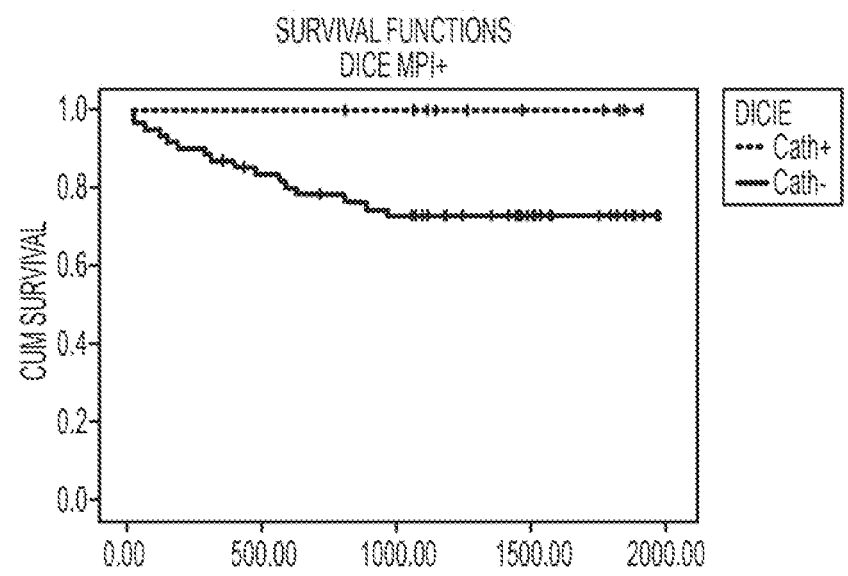
FIG. 7 shows how the modeling approaches described in this document may improve the results of FIG. 6.

FIG. 7 shows Kaplan-Meier plots applied to coronary artery stenosis data using DICE and DICIE. DICE was used to identify patients who are positive for myocardial perfusion deficit (MPI+) and DICIE (described below) was used to improve the catherization data to identify patients with coronary artery disease. In this case, no events occurred in the group below the DICIE defined threshold for coronary artery disease (CAD), while the event rate in the CAD+ group was high and comparable to the event rates noted for the high disease groups of FIG. 6 where the 70% stenosis threshold was chosen (but where 70% of events were missed in this selection of the high disease group).

It should be noted that the processes discussed above are directed toward medical imaging for purposes of an example. The processes may be expanded beyond medical imaging to encompass additional areas of study. For example, DICE may be implemented to improve clinical trials. Currently, there is an extensive research and trial procedure in the pharmaceutical industry. Any errors or problems during those procedures may result in extensive litigation and loss of business for a pharmaceutical company. Pharmaceutical companies often participate in randomized clinical trials (RCTs). An RCT is conceptually simple: a patient population is selected based upon symptoms or risk factors associated with the disease being addressed by the trial drug. Typically, patients are randomized to receive standard of care or the trial drug. After a time period (e.g., 5 years), adverse event rates are analyzed. If the trial drug population has a lower adverse event rate than a population of patients who received previously-developed drugs (or no treatment at all), then the trial is considered a success. A typical RCT may assess about 5,000 subject patients and have a follow-up time of 5 years. If the first RCT was not successful, the chance of making money off the drug is greatly reduced. Society suffers if the benefits of a drug are not discovered due to errors or biases that entered the trial. Additionally, during expanded testing, the results of multiple RCTs may be combined to produce an expanded set of patients, thereby potentially defining a sub-set of patients where problems become evident that were not easily identified in the smaller patient sets. This may put the drug at risk of being removed from the market. Thus, the cost of the initial RCT, the risk of the RCT being overturned, and other factors add to the cost of developing the drug and limit the number of drugs that make it to market.

The DICE process, as described herein, may be used to select a patient population for participation in clinical trials. The process may allow a drug manufacturer to focus an RCT on a population that may benefit from the drug. One assumption in an RCT is that the population selected can be treated as a random sample with equal risk across the population. However, the DICE process may divide the population into a high disease group and a low disease group. Thus, the value of the drug may be determined based upon an evaluation of the high disease group as the low disease group is eliminated. Eliminating the low disease group may greatly improve the study's assessment of how the drug will affect people when only applied to those who need the drug. If the high disease group is isolated out of the random population, the effects of the drug may be evaluated with fewer overall patients over a shorter time period. Additionally, the low disease group may be removed from the trial completely and not fall risk to adverse side effects. Any threshold may be selected to distinguish high disease from low disease, so long as the high disease numbers exceed the low disease numbers. The measurement of "high disease" and "low disease" may be, for example, a physical measurement such as an amount by which an artery is constricted. For example, a threshold of 50% or above may be considered high, while a threshold below 50% may be considered low. Thresholds other than 50% are possible, as described below.

At the start of a trial, knowledge of who is in each group may not be known. As the trial progresses, additional information may become known about the population participating in the trial. For example, patients who experience adverse events may be classified in the high risk group. At some point into the trial (e.g., 6 months), the information may be analyzed to determine what parameters distinguished the high-risk group from the low risk group. For example, it may be determined that patients with a SPECT perfusion deficit are in the high risk group. However, all the patients may not have SPECT images available. The DICE process may be used to identify patients likely to have a SPECT perfusion deficit using non-SPECT criteria (e.g., MRI data) determined based upon various DICE models. Only those predicted to have a SPECT perfusion deficit may be retained in the trial. After several iterations, the trial population progressively condenses to the high risk population.

In some situations, there may be additional conditions to consider. First, it is sometimes the case that for a particular measurement of interest, only data from only one modality is available. Data from a different modality may be available, but if the two modalities did not analyze the same area of interest, then the above process may not precisely apply. If the different modality measures something related, but not the same measurement as the first modality, then the DICE procedure described above may not be sufficient to develop suitable models and thresholds. Second, in medical diagnostic testing, patients who test positive on one modality are also often examined on a second modality. In these two cases a variation on DICE, referred to herein as decisioning informed by combining intermodality entities (DICIE), allows improved decisions to be made.

Figure 8:
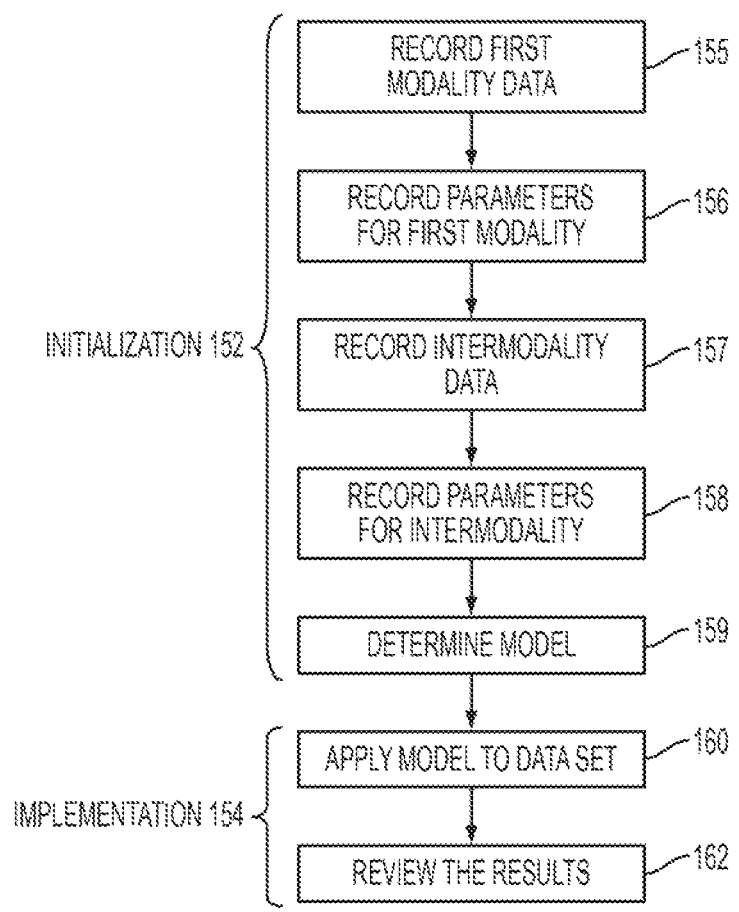
FIG. 8 is a flowchart showing a decision-making process according to an embodiment.

As an example, referring to FIG. 8, DICIE may be used to improve the value of coronary artery stenoses data from a catheterization lab. DICIE may be used on its own, or as an additional step after the application of DICE. With DICIE, data from one test, such as catheterization lab data, may be received 155 and considered first modality data. If the medical professional does not have additional measures of the coronary arteries, then second modality data is not available. Also, if data from additional modalities are available but they correspond too closely with the first modality catheterization results (e.g., coronary catheterization and computed tomography angiography may provide very similar data), both data sets may be influenced by the same bias terms. Thus, reliable corresponding data may not be available.

Doctors typically use the first modality catheterization data to set a threshold to initiate some further action, such as an intervention or medical therapy if the data exceeds the threshold, or no further action if below. Setting the threshold for coronary artery stenosis values involves a compromise, in that if the threshold is set too low (e.g., a 30% stenosis threshold), then too many people are indicated as having severe disease, but a larger number of people who suffer adverse events are captured using this threshold. Alternatively, if the threshold is set too high (e.g., a 70% stenosis threshold) fewer people are indicated as having disease, but most adverse events are missed. Typically, the threshold for action may be set between 50% and 70% stenosis.

Using DICIE, an initialization process 152 may record data 155 and record parameters 156 associated with test results obtained using a first modality (e.g., heart disease test results obtained from SPECT imaging). To improve the value of this test, the initialization process may record data 157 and parameters 158 from a test measuring a related, but not the same, condition. This related data is referred to herein as "intermodality data." For example, if DICIE takes the result of a myocardial perfusion imaging test (e.g. MRI perfusion or SPECT perfusion) as the first modality data, catheterization test results may be intermodality data. There is assumed to be a strong relationship between the first modality data (perfusion test) and the intermodality data (catheterization test). However, while there is a strong relationship, the two modalities measure different physical conditions. It is assumed that patients with a positive perfusion test will have a high-grade coronary artery stenosis that is visible on the catheterization test. To improve the catheterization test in DICIE, a regression analysis may model 159 the binarized result of the first modality and intermodality test and enter in variables that are suspected of causing bias.

The modeling may follow a process such as that shown for DICE in FIG. 2, with intermodality data and parameters substituted for the second modality data and parameters. In our example, we consider the DICE augmented perfusion test as the "target" for modeling, and enter the maximum (max) stenosis of the most highly stenosed coronary artery (max stenosis) along with one or more parameters. In this example, a parameter may be whether or not the patient is on an ACE inhibitor (ACEi) drug, or it may be a physical characteristic such as volume of a cardiac chamber measured using the first modality. The results of the regression model are thresholded by a suitable value, e.g., using the average value of the positive perfusion test. In this example, this model has the form:

$$\text{Predicting perfusion test} = 0.02 + \text{max stenosis} * 0.03 + 0.05 * \text{ACEi} \qquad \text{Equation 2}$$

The threshold is set at 0.26, where max stenosis is the catheterization result, and the value ACEi is 1 if the drug is present, or 0 if it is not. This model and thresholding process achieves two things: 1) it removes the bias (which in this case was the presence of the drug ACEi) and 2) drives the catheterization data into a binarized state, making it more suited to form a threshold decision on disease severity. Other parameters (e.g., parameters other than the presence or absence of ACEi), variables and constants may be used. The results of this model may then be applied to a data set for a new patient 160, such as a patient who has received SPECT or catheterization tests, and the model results may be displayed 162 to a medical professional to determine a course of action for the patient.

A second use of DICIE may be when a second test (e.g., coronary artery catheterization) follows a first test (e.g., myocardial perfusion imaging by MRI or SPECT). In this case, the first test (myocardial perfusion imaging) is preferentially augmented by DICE. From the application of DICIE from Equation 2 above, we know that the catheterization lab results are influenced by the presence of ACEi. However, while the above DICIE equation and threshold do a good job at selecting patients at high risk, it may tend to exaggerate the influence of ACEi, since this is entered as a binarized (0 or 1) number. In the case that the catheterization test is to be performed on patients who are positive by the perfusion test, by definition the test is to be performed on patients who are positive by the perfusion test, by definition the MRI data are available at the time of catheterization. In this case the DICIE model can use the catheterization data and the MRI data to improve the result. In this example, the catheterization data and MRI data are used to model (regression analysis) the perfusion test by MRI:

Predicting perfusion test=0.02+max stenosis*0.03+ 0.07*ESVi+0.2*wall thickness          Equation 3

The threshold is set at 0.26 based on the average perfusion result, where max stenosis is the catheterization results, ESVi is the MRI measured end systolic volume index, and wall thickness is the MRI measured wall thickness of the left ventricle at end systole. Another equation may be used that incorporates the use of ACEi by the patient. In such cases, the model may become binarized. In the case of the equation shown above, the physical attributes of the heart that were likely influenced by the ACEi are specifically incorporated, which makes the result not as highly binarized, and better allows further assessment of the influence of ACEi and other drugs and conditions.

As in DICE, with DICIE there is an initialization phase 152 where the above models and thresholds are generated, and an implementation phase 154 where the models are applied.

The examples included above show the application of DICE and DICIE to nuclear SPECT myocardial perfusion imaging, MRI myocardial perfusion imaging, and coronary angiography, all aimed at assessing the severity of ischemic heart disease in patients with chest pain. The examples also discuss the selection of patient populations for a clinical trial. However, the methods described above are not limited to those fields. Other areas where the DICE and DICIE may be applied include, for example, oncology and diabetes. In oncology, tumors are staged into categories such as stage 1, 2, 3 and 4. These stages are derived from observations in diverse populations. However, the best treatment required to address the tumor for one patient, say in stage 2, might be different for another patient with the same stage of tumor, depending on the background parameters of each patient. Using the modeling approach described above, DICE and DICIE models can be formulated to model one diagnostic test against another. When applied to incorporate the primary and secondary diagnostic variables available from the test that is applied clinically, DICE might indicate that one particular patient with stage 2 cancer requires aggressive treatment while another patient with stage 2 cancer can undergo watchful waiting.

The cardiology and oncology examples typically focus on the use of diagnostic image data, while many diagnostic tests are based on measuring blood levels of a biomarker to indicate the presence and severity of a disease state. Again, there is typically a continuum of values for any given biomarker and typically a threshold is established to indicate that some action should be taken if an individual has a higher or lower value, based on population statistics. As more is known about genetic makeup, different thresholds may be applied based on genetic testing. However, even in these cases, the threshold is set based on population statistics for that group. It is generally the case that wherever the threshold is set, patients below the threshold remain at risk, with events occurring at differing rates as the value decreases. As an example in the case of diabetes, a patient is said to be insulin resistant up to a certain level of fasting blood glucose and diabetic above that threshold. Again, the threshold may be set based on population averages. If two approaches were available to measure variables associate with glucose levels, then DICE could be used to form models of both tests. The DICE model could be used in conjunction with the clinically applied test, which essentially has the effect of setting a threshold to trigger treatment that may be different for different patients.

The DICE and DICIE processes as described herein may be applied to additional fields as well. For example, analyzing statistical data obtained through social networking sites may be improved by using the DICE or DICIE process. Populations of users may be compared and analyzed to determine various groups. Then, once the groups are determined, advertising may be targeted to those groups. With the pace at which social networking sites are growing, targeted advertising is an area of increasing interest. Characteristics associated with a user may be compared to a group model having a population with similar characteristics to determine additional characteristics that may be associated with the user. For example, a user may list that he is a male and attending a certain college, and based upon the DICE and/or DICIE process, a software application may predict that the user is a fan of the local football team. That prediction may be used to target advertising related to the football team to the user. Similarly, a social networking website or application may recommend topics or contacts to various users who have similar interests and thus may be classified into the same group. For example, if a user lists she is a lawyer located in Pennsylvania, the social networking site may analyze a model of lawyers in Pennsylvania and predict special interest groups the user may want to join.

Similarly, the DICE and DICIE processes described herein may be used to train people who regularly perform decision making. For example, security officers may be trained based upon historical data to make more informed decisions. To establish a set of historical data, security officers in an airport may be separated into two or more security teams. Decisions related to suspects may be recorded, examined and compared between the multiple security teams. Based upon various criteria used to make a specific decision (e.g., why did one security team identify a suspect that another security team did not), the decision-making process used by all security teams may be standardized such that all security teams rely on the same criteria for identifying suspects.

Additional applications may include athletic coaches or officials identifying talented recruits, human resource personnel selecting candidates for a job, education specialists designing a teaching curriculum, and other fields where human judgment is based upon only a select set of concrete evidence.

Figure 9:
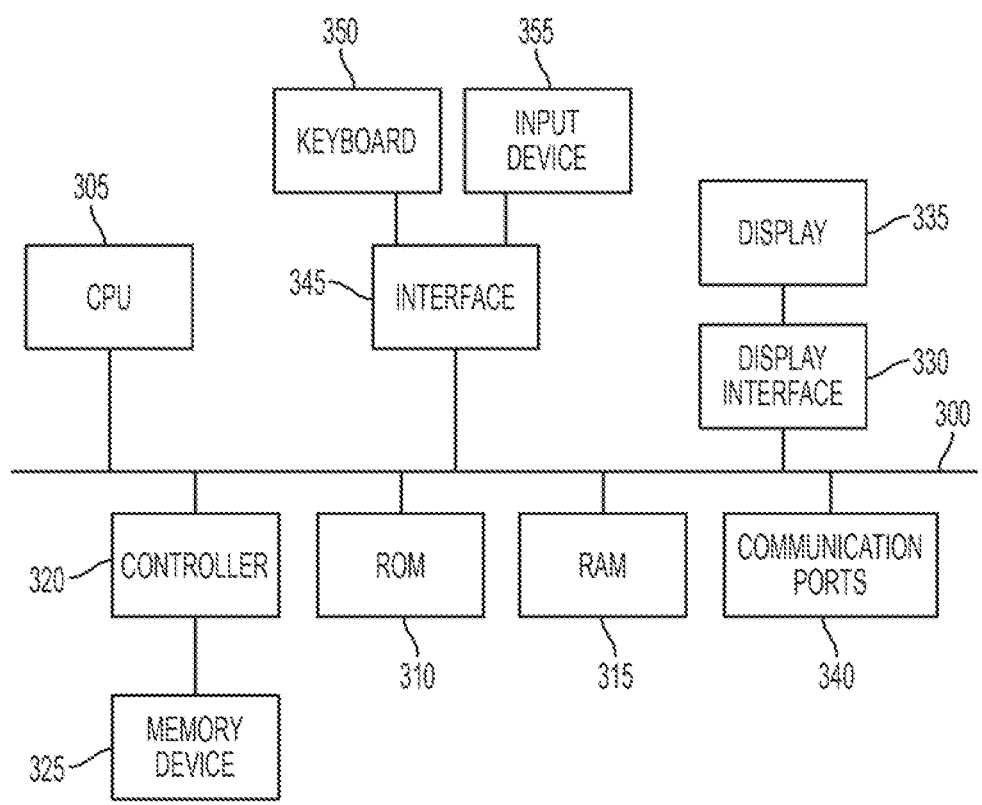
FIG. 9 illustrates various elements of a computing device for implementing various methods and processes described herein.

FIG. 9 depicts a block diagram of internal hardware that may be used to contain or implement various components to perform the DICE and/or DICIE processes illustrated the previous figures. A bus 300 serves as the main information highway interconnecting the other illustrated components of the hardware. CPU 305 is the central processing unit of the system, performing calculations and logic operations required to execute a program. CPU 305, alone or in conjunction with one or more of the other elements disclosed in FIG. 9, is an illustration of a processing device, computing device or processor as such terms are used within this disclosure. Read only memory (ROM) 310 and random access memory (RAM) 315 constitute examples of memory devices.

A controller 320 interfaces with one or more optional memory devices 325 to the system bus 300. These memory devices 325 may include, for example, an external or internal DVD drive, a CD ROM drive, a hard drive, flash memory, a USB drive or the like. As indicated previously, these various drives and controllers are optional devices. Additionally, the memory devices 325 may be configured to include individual files for storing any software modules or instructions, auxiliary data, common files for storing groups of results or auxiliary, or one or more databases for storing the result information, auxiliary data, and related information as discussed above.

Program instructions, software or interactive modules for performing the DICE process as discussed above may be stored in the ROM 310 and/or the RAM 315. Optionally, the program instructions may be stored on a tangible computer readable medium such as a compact disk, a digital disk, flash memory, a memory card, a USB drive, an optical disc storage medium, and/or other recording medium.

An optional display interface 330 may permit information from the bus 300 to be displayed on the display 335 in audio, visual, graphic or alphanumeric format. The information may include information related various data sets. Communication with external devices may occur using various communication ports 340. A communication port 340 may be attached to a communications network, such as the Internet or an intranet.

The hardware may also include an interface 345 which allows for receipt of data from input devices such as a keyboard 350 or other input device 355 such as a mouse, a joystick, a touch screen, a remote control, a pointing device, a video input device and/or an audio input device.

Several of the above-disclosed and other features and functions, or alternatives thereof, may be combined into many other different systems or applications. Various presently unforeseen or unanticipated alternatives, modifications, variations or improvements therein may be subsequently made by those skilled in the art, each of which is also intended to be encompassed by the disclosed embodiments.

What is claimed is:

1. A method, comprising:
    receiving, by a processor, a medical test result, having a numeric value and representing a measured observation of a portion of a patient's body using a first medical testing modality;
    receiving, by the processor, at least one background parameter of the patient representing a pre-existing status of the patient;
    identifying a potential recommendation for a medical course of action;
    accessing, by the processor, a decision-making model comprising a plurality of thresholds, where each of the thresholds represents at least one background parameter and a level at which a majority of historic patients in a given set of historic patients was recommended for the medical course of action based on correlated test results for the given set of historic patients from both the first medical testing modality measuring a first determinant that affects an outcome of a disease with an unknown state and a second medical testing modality measuring a second determinant that affects the outcome of the disease, where the second medical testing modality is different than the first medical testing modality and the second determinant is the same as the first determinant;
    selecting, by the processor, a threshold that corresponds to the background parameter of the patient;
    comparing, by the processor, the numeric value of the medical test result to the selected threshold;
    determining, by the processor, that the numeric value of the medical test result equals or exceeds the selected threshold; and
    in response to the determining, recommending, by the processor, the medical course of action.

2. The method of claim 1, further comprising developing the decision-making model by receiving, by a computing device, a first data set of medical testing results corresponding to tests performed on the given set of historic patients using the first medical testing modality;
    receiving, by the computing device, a first set of background parameters corresponding to the given set of historic patients;
    receiving, by the computing device, a second data set of medical testing results corresponding to tests performed on the given set of historic patients using the second medical testing modality;
    receiving, by the computing device, a second set of background parameters corresponding to the given set of historic patients;
    determining, by the computing device, the decision-making model based upon the first data set, the second data set, the first set of background parameters, and the second set of background parameters, such that the decision-making model includes a plurality of parameter-dependent thresholds for medical testing results from either or both of the first medical testing modality and the second medical testing modality.

3. The method of claim 1, wherein the first medical testing modality and the second medical testing modality comprise tests that each measure a same observation of a portion of a patient's body.

4. The method of claim 1, wherein the first medical testing modality and the second medical testing modality comprise tests that measure different observations of a portion of a patient's body.

5. The method of claim 1, wherein:
    the first medical testing modality and second medical testing modality comprise cardiac nuclear single photon emission computed tomography and magnetic resonance imaging;
    the threshold is a predicted result of a test performed using the second medical testing modality; and
    the medical course of action is treatment of a perfusion deficit.

6. The method of claim 1, wherein the background parameter comprises at least one of: an indication that the patient is taking a prescription drug; and data corresponding to the patient's blood pressure.

7. The method of claim 1, further comprising:
    receiving, by the processor, a plurality of additional medical test results for a plurality of additional patients, wherein each test result corresponds to the first medical testing modality;

receiving, by the processor, at least one background parameter for each of the additional patients;
identifying a potential recommendation for a medical course of action;
accessing, by the processor, the decision-making model;
selecting, for each additional patient of the plurality of additional patients, one of the plurality of thresholds that corresponds to the background parameter of the additional patient,
comparing, by the processor, the numeric value of the medical test result for each additional patient respectively to the threshold which was previously selected therefore,
determining, by the processor, a subset of the additional patients for whom the numeric value of the medical test result equals or exceeds the selected threshold, and
in response to the determining, recommending, by the processor, the medical course of action for the subset.

8. A method, comprising:
receiving, by a processor, a plurality of medical test result for a plurality of patients, each medical test result representing a measured medical observation of the medical test result's corresponding patient using a first medical testing modality;
receiving, by the processor, at least one background parameter for each patient, the background parameter representing a pre-existing status of each patient of the plurality of patients;
accessing, by the processor, a decision-making model comprising a plurality of thresholds, wherein each of the thresholds represents at least one background parameter and is based on correlated test results for a given set of individuals from both the first medical testing modality measuring a first determinant that affects an outcome of a disease with an unknown state and a second medical testing modality measuring a second determinant that affects the outcome of the disease, where the second medical testing modality is different than the first medical testing modality and the second determinant is the same as the first determinant;
selecting, by the processor, a background parameter-dependent threshold;
identifying, from the plurality of patients, a subset of patients whose medical test results equal or exceeds the selected threshold and whose background parameters meet the background parameter on which the selected threshold depends; and
in response to the determining, recommending, by the processor, the subset of patients for participation in additional testing.

9. The method of claim 8, further comprising developing the decision-making model by
receiving, by a computing device, a first data set of medical testing results corresponding to tests performed on the given set of individuals using the first medical testing modality;
receiving, by the computing device, a first set of background parameters corresponding to the given set of individuals;
receiving, by the computing device, a second data set of medical testing results corresponding to tests performed on the given set of individuals using the second medical testing modality;
receiving, by the computing device, a second set of background parameters corresponding to the given set of individuals; and
determining, by the computing device, the decision-making model based upon the first data set, the second data set, the first set of background parameters, and the second set of background parameters, such that the decision-making model includes a plurality of parameter-dependent thresholds for medical testing results from either or both of the first medical testing modality and the second medical testing modality.

10. The method of claim 8, wherein the first medical testing modality and the second medical testing modality comprise tests that each measure a same observation of a portion of a patient's body.

11. The method of claim 8, wherein the first medical testing modality and the second medical testing modality comprise tests that measure different observations of a portion of a patient's body.

12. The method of claim 8, wherein the background parameter comprises at least one of an indication that the patient is taking a prescription drug; and data corresponding to the patient's blood pressure.

13. A recommendation system, comprising:
a processor;
a tangible, processor-readable memory holding program instructions that instruct the processor to:
receive a medical test result having a numeric value and representing a measured observation of a portion of a patient's body using a first medical testing modality;
receive at least one background parameter of the patient, the parameter representing a pre-existing status of the patient;
identify a potential recommendation for a medical course of action;
access a decision-making model, comprising a plurality of thresholds, wherein each threshold of the plurality of thresholds represents at least a level at which a majority of historic patients in a given set of historic patients was recommended for the medical course of action based on correlated test results for the given set of historic patients from both the first medical testing modality measuring a first determinant that affects an outcome of a disease with an unknown state and a second medical testing modality measuring a second determinant that affects the outcome of the disease, where the second medical testing modality is different than the first medical testing modality and the second determinant is the same as the first determinant;
select a threshold from the plurality of thresholds that corresponds to the background parameter of the patient;
compare the numeric value of the medical test result to the threshold which was previously selected;
determine that the numeric value of the medical test result equals or exceeds the threshold which was previously selected; and
in response to the determining, recommend the medical course of action.

14. The system of claim 13, wherein the tangible, processor-readable memory also holds program instructions that instruct the processor to develop the decision-making model by:
receiving a first data set of medical testing results corresponding to tests performed on the given set of historic patients using the first medical testing modality;
receiving a first set of background parameters corresponding to the given set of historic patients;

receiving a second data set of medical testing results corresponding to tests performed on the given set of historic patients using the second medical testing modality;

receiving a second set of background parameters corresponding to the given set of historic patients; and determining the decision-making model based upon the first data set, the second data set, the first set of background parameters, and the second set of background parameters, such that the decision-making model includes a plurality of parameter-dependent thresholds for medical testing results from either or both of the first medical testing modality and the second medical testing modality.

15. The system of claim 13, wherein the first medical testing modality and the second medical testing modality each measure a same observation of a portion of a patient's body, and the course of action comprises a medical course of action.

16. The system of claim 13, wherein the first medical testing modality and the second medical testing modality comprise tests that measure different observations of a portion of a patient's body.

17. The system of claim 13, wherein the tangible, processor-readable memory also holds program instructions that instruct the processor to:

receive a plurality of additional medical test results for a plurality of additional patients, wherein each test result corresponds to the first medical testing modality;

receive at least one background parameter each additional patient of the plurality of additional patients;

identify a potential recommendation for a medical course of action;

access the decision-making model:

select, for each the additional patient, a threshold from the plurality of thresholds that corresponds to the background parameter of the additional patient;

compare the numeric value of the medical test result for the additional patient to the threshold which was previously selected;

determine a subset of the additional patients for whom the numeric value of the medical test result equals or exceeds the threshold; and in response to the determining, recommend the medical course of action for the subset of the additional patients.

18. A recommendation system, comprising:

a processor;

a tangible, processor-readable memory holding program instructions that instruct the processor to:

receive a test result having a numeric value and representing a measured observation of a portion of a subject using a first testing modality;

receive at least one background parameter of the subject;

identify a potential recommendation for a course of action for the subject;

access a decision-making model comprising a plurality of thresholds, wherein each threshold of the plurality of thresholds represents at least one background parameter and a level at which a majority of historic subjects in a set of subjects was recommended for the course of action based on correlated test results for the set of subjects from both the first testing modality measuring a first determinant that affects an outcome of a disease with an unknown state and a second testing modality measuring a second determinant that affects the outcome of the disease, where the second medical testing modality is different than the first medical testing modality and the second determinant is the same as the first determinant;

select a threshold that corresponds to the background parameter of the subject;

compare the numeric value of the test result to the threshold which was previously selected;

determine that the numeric value of the test result equals or exceeds the selected threshold which was previously selected; and in response to the determining, recommend the course of action.

19. The system of claim 18, wherein the tangible, processor-readable memory also holds program instructions that instruct the processor to develop the decision-making model by:

receiving a first data set of testing results corresponding to tests performed on the set of subjects using the first testing modality;

receiving a first set of background parameters corresponding to the set of subjects;

receiving a second data set of testing results corresponding to tests performed on the set of subjects using the second testing modality;

receiving a second set of background parameters corresponding to the set of subjects; and determining the decision-making model based upon the first data set, the second data set, the first set of background parameters, and the second set of background parameters, such that the decision-making model includes a plurality of parameter-dependent thresholds for testing results from either or both of the first medical modality and the second testing modality.

20. The system of claim 18, wherein the tangible, processor-readable memory also holds program instructions that instruct the processor to:

receive a plurality of additional test results for a plurality of additional subjects, wherein each additional test result corresponds to the first testing modality;

receive at least one background parameter for each additional subject of the plurality of additional subjects;

identify a potential recommendation for a course of action;

access the decision-making model:

select, for each the additional subject, a threshold from the plurality of thresholds that corresponds to the background parameter of the subject;

compare the numeric value of the test result for each the additional subject to the threshold;

determine a subset of the additional subjects for whom the numeric value of the test result equals or exceeds the threshold; and in response to the determining, recommend the course of action for the subset of the additional subjects.

* * * * *